(12) United States Patent
Nashtaali et al.

(10) Patent No.: US 10,329,610 B2
(45) Date of Patent: Jun. 25, 2019

(54) PAIRED-END SEQUENCING METHOD

(71) Applicants: Damoun Nashtaali, Tehran (IR); Seyed Abolfazl Motahari, Tehran (IR); Babak Hossein Khalaj, Tehran (IR)

(72) Inventors: Damoun Nashtaali, Tehran (IR); Seyed Abolfazl Motahari, Tehran (IR); Babak Hossein Khalaj, Tehran (IR)

( * ) Notice: Subject to any disclaimer, the term of this patent is extended or adjusted under 35 U.S.C. 154(b) by 0 days.

(21) Appl. No.: 15/667,269

(22) Filed: Aug. 2, 2017

(65) Prior Publication Data
US 2018/0030529 A1 Feb. 1, 2018

Related U.S. Application Data

(60) Provisional application No. 62/370,069, filed on Aug. 2, 2016.

(51) Int. Cl.
*C12Q 1/68* (2018.01)
*G06F 19/22* (2011.01)
*C12Q 1/6869* (2018.01)
*G16B 30/00* (2019.01)

(52) U.S. Cl.
CPC ........... *C12Q 1/6869* (2013.01); *G16B 30/00* (2019.02)

(58) Field of Classification Search
CPC ............ C12Q 1/6869; C12Q 2535/122; C12Q 2537/165
See application file for complete search history.

(56) References Cited

FOREIGN PATENT DOCUMENTS

WO    WO2013177086 A1 * 11/2013 ............... C12Q 1/68

* cited by examiner

*Primary Examiner* — David C Thomas
(74) *Attorney, Agent, or Firm* — NovoTechIP Imternational PLLC

(57) ABSTRACT

A paired-end sequencing method for sequencing a string of oligonucleotides is disclosed. The method includes preparing a template that includes a substrate with a plurality of wells. Each well includes a pair of strands, formed of a forward strand and a corresponding reverse strand, from the string of oligonucleotides. Each pair of strands are sequenced simultaneously to obtain a reads pairs set, where each reads pair includes a read and a corresponding read-pair. The reads pairs set is processed by generating a sequences pairs set, where each sequences pair has a read sequence and a read-pair sequence respective to a pair of reads of the set of pairs of reads, mapping the sequences pairs set along a reference genome, and re-sequencing the mapped sequences pairs set to obtain the sequence of the string of oligonucleotides.

15 Claims, 10 Drawing Sheets

Specification includes a Sequence Listing.

SEQUENCE LISTING

```
<160> NUMBER OF SEQ ID NOS: 3

<210> SEQ ID NO 1
<211> LENGTH: 10
<212> TYPE: DNA
<213> ORGANISM: Unknown
<220> FEATURE:
<223> OTHER INFORMATION: An example sequence used in the paired-end
      sequencing method presented in Figure 4 of the present application

<400> SEQUENCE: 1
gaccagccgt                                                          10

<210> SEQ ID NO 2
<211> LENGTH: 10
<212> TYPE: DNA
<213> ORGANISM: Unknown
<220> FEATURE:
<223> OTHER INFORMATION: An example sequence used in the paired-end
      sequencing method presented in Figure 4 of the present application

<400> SEQUENCE: 2
atctctccgg                                                          10
```

```
<210> SEQ ID NO 3
<211> LENGTH: 10
<212> TYPE: DNA
<213> ORGANISM: Unknown
<220> FEATURE:
<223> OTHER INFORMATION: An example sequence used in the paired-end
      sequencing method presented in Figure 4 of the present application

<400> SEQUENCE: 3
gaccatccgt                                                                10
```

PAIRED-END SEQUENCING METHOD

CROSS-REFERENCE TO RELATED APPLICATION

This application claims the benefit of priority from pending U.S. Provisional Patent Application Ser. No. 62/370,069, filed on Aug. 2, 2016, and entitled "A NEW FAST AND LOW-COST PAIRED-END SEQUENCING METHOD," which is incorporated herein by reference in its entirety.

TECHNICAL FIELD

The present disclosure generally relates to methods for sequencing a string of oligonucleotides, such as DNA, and particularly to a method for DNA paired-end sequencing. The method further relates to a method for simultaneous paired-end sequencing of fragments and their pairs of the string of oligonucleotides.

BACKGROUND

New technologies for DNA sequencing and extracting human DNA sequences such as Next Generation Sequencing (NGS) were gradually developed to achieve higher throughput for extraction of genomic information at a lower cost. NGS technologies consist of three main stages: template preparation, base calling (which is mostly based on imaging) and processing. In the template preparation stage, DNA fragments are first randomly broken to smaller fragments, and such fragments are attached to solid surface of a template platform. Following this step, two different approaches may be used for preparing templates: (a) amplification of a single molecule and (b) single molecule preparation. Because detection of the signal corresponding to a single molecule can be challenging, amplification of a single molecule is the step commonly adopted in many practical NGS methods, such as in Illumina technology. Subsequent to the template preparation stage, an observed signal must be detected for the base calling. The detected signal may be the temperature, pH, or intensity of fluorescence photons. After detecting nucleotides, generated reads must be processed at the last stage. The processing stage may consist of alignment or assembly of fragments methods which can also exploit an existing reference genome.

In order to resolve repeats on the genome or to determine Structural Variations (SVs) between target and reference genomes, paired-end sequencing is being developed. In paired-end sequencing, larger fragments of DNA samples can be used. After a bio-chemical process, two paired sequences are read by sequencer machine from the fragment with a known insert size between them. In the traditional scheme, the paired-end sequencing process is performed for each one of two sequences independently. Consequently, after bounding these larger fragments to the substrate and amplification step, an enzyme is used to detach reverse stands from the substrate. A sequencing procedure is then started for the forward strands. Following the sequencing of the forward stands, DNA polymerase is again added to the solution in order to construct reverse stands. An enzyme is also added to detach the forward stands and the sequencing of the reverse strands is carried out. It can be understood that current paired-end sequencing methods require an extended period of time and involve the consumption of large amounts of material.

Hence, there is a need for a method for sequencing both DNA strands (i.e., the forward strand and the reverse strand) simultaneously. In such a scheme, only half of the traditional method's materials would be consumed. In addition, the time needed for the sequencing process to occur may be halved relative to traditional paired-end sequencing methods.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes a paired-end sequencing method for sequencing a string of oligonucleotides. The method includes preparing a template, the template including a substrate with a plurality of wells. Each well contains a pair of strands from the string of oligonucleotides, where each pair of strands includes a forward strand and a corresponding reverse strand. The method further includes sequencing the pair of strands simultaneously within each well to obtain a reads pairs set. Each reads pair includes a read and a corresponding read-pair associated with a well, and the read and the corresponding read-pair include a pre-defined insert size distance from one another. Furthermore, the method includes processing the reads pairs set, the processing including generating a sequences pairs set, where each sequences pair includes a read sequence and a read-pair sequence corresponding to a reads pair of the reads pairs set, mapping the sequences pairs set along a reference genome, and re-sequencing the mapped sequences pairs set to obtain a sequence of the string of oligonucleotides.

The above general aspect may include one or more of the following features. In one example, preparing the template includes shearing a number of copies of the string of oligonucleotides to obtain a plurality of forward strands, placing each forward strand within its own well, amplifying each forward strand, thereby obtaining a corresponding reverse strand within each well, separating each forward strand from its corresponding reverse strand within each well to obtain a pair of strands within each well, and/or the fluorescent tagging of the pair of strands within each well. In some implementations, amplifying each forward strand occurs by a cloning based technique or a free-cloning based technique. In another example, sequencing the pair of strands simultaneously includes detecting fluorescence photons of oligonucleotide bases along the forward strand and the corresponding reverse strand simultaneously using a detector with at least two channels for wavelength filtering in order to obtain the reads pairs set. In some cases, the detector includes either two or four channels for wavelength filtering. In addition, in one example, generating the sequences pairs set includes detecting each pair of oligonucleotide bases along both the read and the corresponding read-pair, where each pair of oligonucleotide bases is classified within one of three classes. The three classes include: a unique class U, including a set of pairs of oligonucleotide bases with a unique possibility for each oligonucleotide base, a double class D, including a set of pairs of oligonucleotide bases with two possibilities for each oligonucleotide base, and a triple class T, including a set of pairs of oligonucleotide bases with three possibilities for each oligonucleotide base. In some implementations, mapping the sequences pairs set along the reference genome includes searching for each sequences pair of the sequences pairs set along the reference genome by considering oligonucleotide bases of the sequences pair that are classified in the unique class U and locating the read sequence and read-pair sequence of the searched sequences pair along the reference genome, aligning the located sequences pair along the reference genome if the read sequence and the read-pair sequence are associated with a distance substantially equal to the pre-defined insert size distance, and accepting the aligned sequences pair along the reference genome if oligonucleotide bases of the sequences pair that are classified in the double class D or in the triple class T are consistent with corresponding oligonucleotide bases of the reference genome.

In another example, mapping the sequences pairs set along the reference genome includes determining three sets for each sequences pair $r_i$ from the sequences pairs set r $\{r_1, r_2, \ldots, r_i, \ldots, r_N, r_1^*, \ldots, r_N^*\}$, the three sets including the unique class $U(r_i)$, the double class $D(r_i)$ and the triple class $T(r_i)$, initializing a set S $\{S_{(r1)}, S_{(r2)}, \ldots, S_{(ri)}, \ldots, S_{(rN)}\}$ equal to zero (Ø), where $S_{(ri)}$ includes the mapped sequences pairs set that includes a set of strings and corresponding locations on the reference genome for each read sequence $r_i$, generating a set $\hat{r}$ $\{(\hat{r}_1, \ldots, \hat{r}_i, \ldots, \hat{r}_N\}$ respective to the set r by retaining the set U ($r_i$) and setting other oligonucleotide bases as N, aligning the set $\hat{r}$ to the reference genome using an algorithm based on a Burrows-Wheeler Transform (BWT) to find the mapped sequences pairs set for $r_i$, updating the set S by updating each $S_{(ri)}$. The update can include sorting and saving the mapped sequences pairs set for each $r_i$ as $S_{(ri)}$, where the location of a $m^{th}$ string is represented by $1_{S(m)}$, and m is within a set of $\{1, \ldots, m, \ldots, |S|\}$ and $|S|$ the size of $S_{(ri)}$. In addition, the mapping can include setting a parameter E to be equal to a Hamming distance of each S(j) and $r_i$ in $D(r_i)$ and $T(r_i)$ locations if the distance between a $1_{S(j)}$ and the next $1_{S(k)}$ is≥D−Δ, where j is within $\{1, \ldots, |S|\}$, k is within $\{j+1, \ldots, |S|\}$, D represents an average of the pre-defined insert size distance, and A represents a variance of the pre-defined insert size distance, and adding $\{(S_{(j)}, 1_{S(j)}), (S_{(k)}, 1_{S(k)})\}$ to $S_{(ri)}$ if E≤2, where updating the $S_{(ri)}$ ceases if the distance between a $1_{S(k)}$ and next $1_{S(k)}$ is>D+Δ.

In some cases, re-sequencing of the mapped sequences pairs set includes denoting oligonucleotide bases of the mapped sequences pairs set, where the denoting includes: denoting a set of oligonucleotide bases within the mapped read sequences of the mapped sequences pairs set that are aligned to a first oligonucleotide base of the reference genome as a first set of c-bases, and denoting a set of oligonucleotide bases within the mapped read-pair sequences of the mapped sequences pairs set that are aligned to a second oligonucleotide base of the reference genome as a first set of cp-bases, assigning a first subset of the first set of c-bases to the first oligonucleotide base of the reference genome and a second subset of the first set of cp-bases to the second oligonucleotide base of the reference genome, where the first subset includes the most probable oligonucleotide bases that are associated with a maximum vote among the unique class U, the double class D, and the triple class T for an oligonucleotide base of the first set of c-bases, and where the second subset includes the most probable oligonucleotide bases that are associated with a maximum vote among the unique class U, the double class D, and the triple class T for an oligonucleotide base of the first set of cp-bases. In addition, there can be a determining of the sequence of the string of oligonucleotides, the determining including: setting a first string oligonucleotide base of the string of oligonucleotides equal to the first oligonucleotide base if the first subset is uniquely assigned to the first oligonucleotide base of the reference genome, and setting a second string oligonucleotide base of the string of oligonucleotides equal to the second oligonucleotide base if the second subset is uniquely assigned to the second oligonucleotide base of the reference genome.

In another example, re-sequencing the mapped sequences pairs set includes a procedure of: creating a set $R_g$ of the c-bases and a set $R_g^*$ of the cp-bases for each oligonucleotide base g of the reference genome, where g is within (1, ..., G), and G represents a length of the reference genome, setting a set $V_g$ of maximum voted c-bases of the $R_g$; setting a re-sequenced oligonucleotide base g equal to the oligonucleotide base g if the $|V_g|=1$, wherein $|V_g|$ represents size of $V_g$, and removing oligonucleotide base $V_h$ from $V_g$ if $|V_h|=1$ and $|V_g|\neq 1$, where: $V_h$ includes a plurality of sets for each h, h includes the corresponding oligonucleotide base within all read-pair sequences corresponding to read sequences including oligonucleotide base g, the procedure iterates for all oligonucleotide bases within the reference genome if no update occurs in $V_g$, $V_g$ is assigned to base g, and the procedure ceases if no new oligonucleotide base is updated or all oligonucleotide bases are uniquely determined. In another example, the string of oligonucleotides and the reference genome include an equal number of oligonucleotide bases represented as G. In different implementations, the pre-defined insert size distance includes a length of oligonucleotide bases in a range of 100 oligonucleotide bases to more than 1000 oligonucleotide bases. In addition, each reads pair of the reads pairs set can include L oligonucleotide bases, wherein L includes at least 50 oligonucleotide bases.

Other systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the following claims.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1:
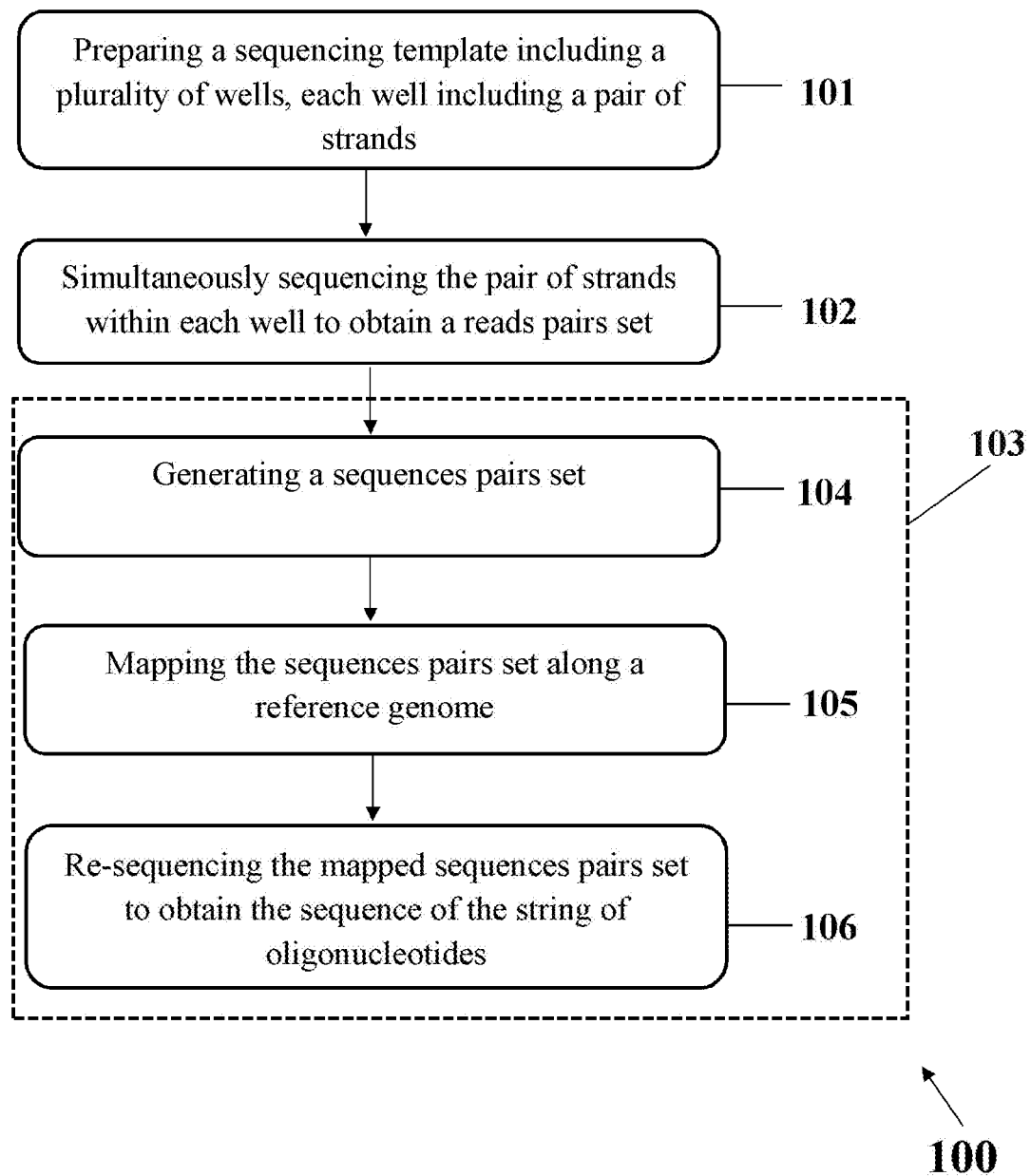
FIG. 1 illustrates an implementation of a paired-end sequencing method for sequencing a string of oligonucleotides.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Systems and methods directed to a paired-end sequencing are disclosed. The method involves sequencing a string of oligonucleotides, such as for example, a target DNA or RNA. A number of fragments of the string of oligonucleotides are sequenced, a number of reads (i.e., nucleotide sequences) and their pairs are generated at substantially the same time, and reads are extracted from a reference genome's information. In contrast, in traditional methods, such as those used by Illumina technology, sample fragments are first amplified and reverse strands are detached from the platform. After sequencing the forward strands, amplification is again performed, the forward strands are detached from the platform, and the reverse strands are sequenced. The method disclosed herein is designed to read both forward and reverse strands at substantially the same time. In some cases this method may result in the return of less information, but these losses may be recovered by use of the reference genome.

Thus, the disclosed paired-end sequencing method overcomes many shortcomings of the conventional paired-end DNA sequencing methods, which generally require a large amount of material over a longer period of time. In the paired-end sequencing method described herein, the required time and resources/materials for sequencing a string of oligonucleotides is greatly decreased. In one implementation, the total sequencing time and the amount of material consumed is decreased by a factor of two relative to traditional methods. In addition, the methods described herein may benefit from a reference genome and other sequenced reads and information, in contrast with the traditional scheme (such as, for example, Illumina sequencing technology). In some implementations, the present method can utilize a reference genome and/or other fragments and information while sequencing a string of oligonucleotides, such as a target DNA or RNA.

As will be detailed below, the disclosed methods can provide a process for simultaneous sequencing of a number of reads and their pairs from a string of oligonucleotides. The method can also provide an algorithm for mapping the outputted reads of the provided method to a reference genome where it may map paired-end reads to the reference genome. In this case, each oligonucleotide base of the read and its corresponding oligonucleotide base in the read-pair have one, two, or three possible options with relocation of two oligonucleotide bases between the read and its reed-pair. The method also provides an algorithm for re-sequencing the string of oligonucleotides with the paired-end reads that are incompletely mapped.

Referring to FIG. 1, one implementation of a paired-end sequencing method for sequencing a string of oligonucleotides is presented. In the implementation of FIG. 1, the method includes a first step 101 of preparing a template. In different implementations, the template may include a substrate with a plurality of wells. Each well may further include a pair of strands, and each of the pair of strands may include a forward strand and a corresponding reverse strand from the string of oligonucleotides. In addition, each reads pair may include a read and a corresponding read-pair associated with a well of the plurality of wells. Furthermore, in some implementations, the read and the corresponding read-pair may have a pre-defined insert size distance from one another.

In a second step 102, each strand of the pair of strands within each well is simultaneously (or substantially simultaneously) sequenced to obtain a set of pairs of reads ("reads pairs set"). A third step 103 involves processing the reads pairs set. In some implementations, processing the reads pairs set may include additional steps, such as generating a set of pairs of sequences ("sequences pairs set") in a fourth step 104, mapping the sequences pairs set along a reference genome in a fifth step 105. The mapped sequences pairs set can then be re-sequenced in order to obtain a sequence of the string of oligonucleotides in a sixth step 106. In one implementation, each pair of sequences may include a read sequence and a read-pair sequence associated with each reads pair in the reads pairs set.

Furthermore, in some implementations, the string of oligonucleotides and the reference genome may have approximately the same length. In one implementation, there is also an equal number of oligonucleotide bases in each that may be represented as G. In some implementations, the read and the corresponding read-pair may include a pre-defined insert size distance from one another along the string of oligonucleotides. This distance can cover a length of oligonucleotide bases in a range of about 100 oligonucleotide bases to more than about 1000 oligonucleotide bases. In one example, the forward strand and the corresponding reverse strand may be associated with a length size in a range between about 100 kb to about 10000 kb. Moreover, in some implementations, each reads pair of the set of pairs of reads may include L oligonucleotide bases that may include at least 50 oligonucleotide bases.

Figure 2:
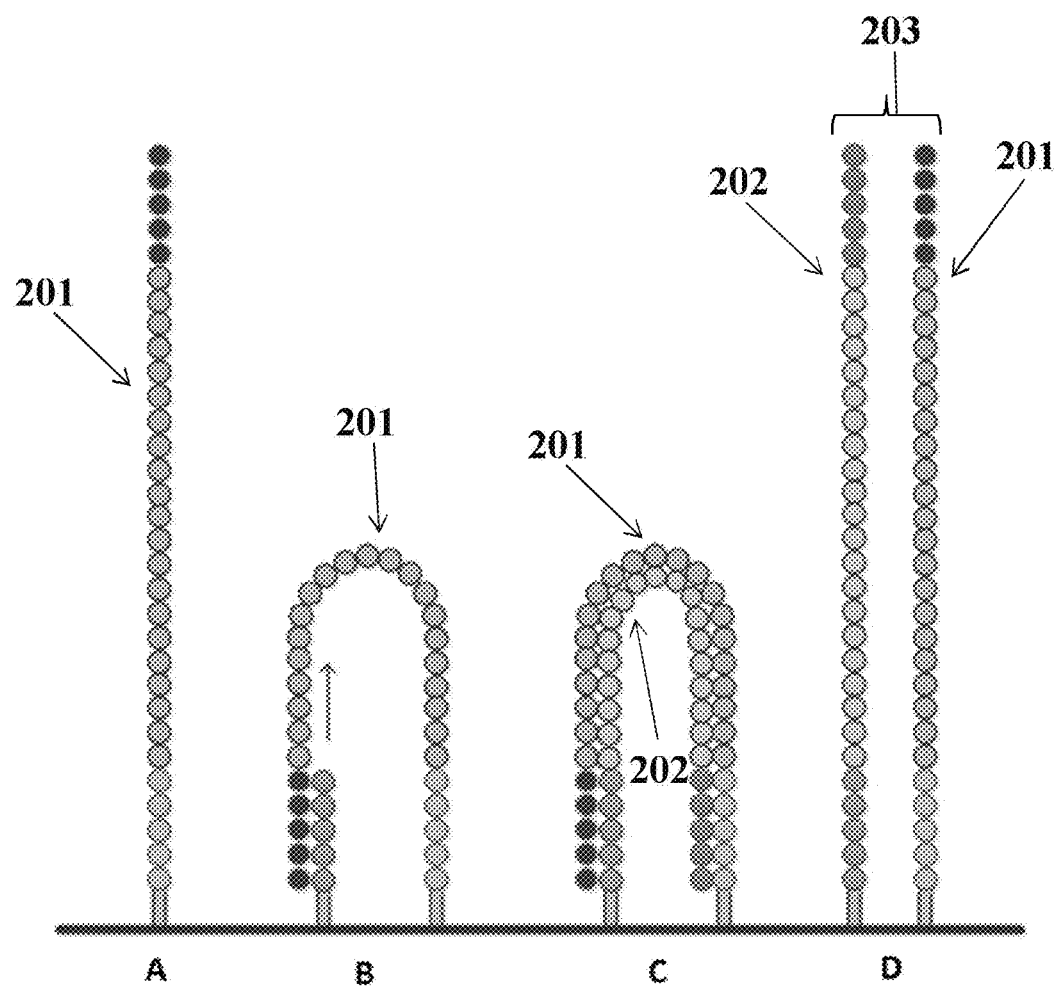
FIG. 2 illustrates a schematic view of an implementation of preparing a template for paired-end sequencing.

For purposes of clarity to the reader, additional details regarding the first step 101 of the method 100 are provided by way of the illustration of FIG. 2. For example, the process associated with preparing the template in the first step 101 may include shearing a number of the strings of oligonucleotides to obtain a plurality of forward strands. This can occur by attaching each forward strand 201 onto one well of the plurality of wells that is embedded on the substrate (part A), and then amplifying each forward strand 201 attached within each well in order to obtain a corresponding reverse strand 202 within each well (part B and C).

Following this step, the process includes separating the forward strand 201 and the corresponding reverse strand 202 within each well to obtain an attached pair of strands 203 within each well (part D), and fluorescent tagging of the attached pair of strands 203 within each well. In some implementations, the prepared template may be used for paired-end sequencing of the attached pair of strands 203 within each well at the same or substantially same time.

Furthermore, in some implementations, each forward strand 201 that is attached within each well may be amplified using a cloning based technique or a free-cloning based technique. Such amplification techniques may be used to construct the corresponding reverse strand 202 to each forward strand 201. In one example, the forward strand 201 and the corresponding reverse strand 202 within each well may be separated by heating.

As noted above, in second step 102, the pair of strands within each well may be sequenced simultaneously. For example, a sequencing machine can be used to obtain a set of pairs of reads, which may include a reads pair that are sequenced for each well. Each reads pair may include a read and a corresponding read-pair associated to a well of the plurality of wells.

In some implementations, each read and its corresponding read-pair may have a pre-defined insert size distance from one another along the respective pair of strands. Thus, in some implementations, each read and the corresponding read-pair may have a pre-defined known insert size distance from one another along the string of oligonucleotides.

In addition, in some implementations, the pair of strands within each well may be sequenced simultaneously. This can occur by detection of fluorescence photons of oligonucleotide bases along the forward strand and the corresponding reverse strand at the same time using a detector. In some implementations, the detector may include at least two channels for wavelength filtering. In one implementation, the detector includes four channels.

Figure 3A:
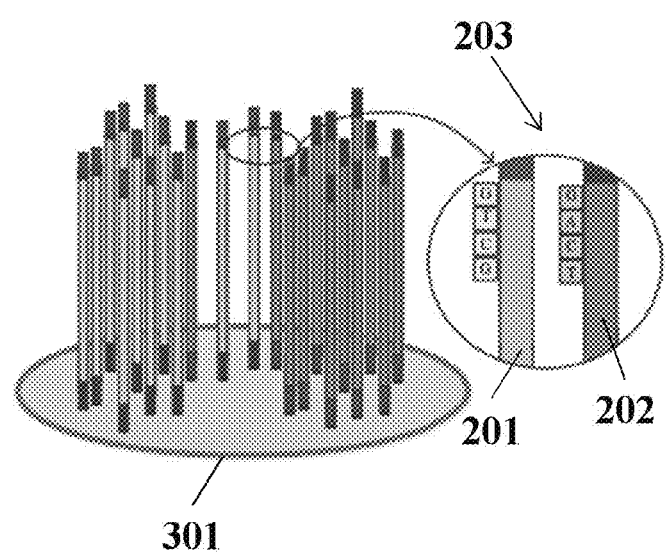
FIG. 3A illustrates an implementation of a well and a pair of strands of the string of oligonucleotides from the template prepared for simultaneous paired-end sequencing.
Figure 3B:
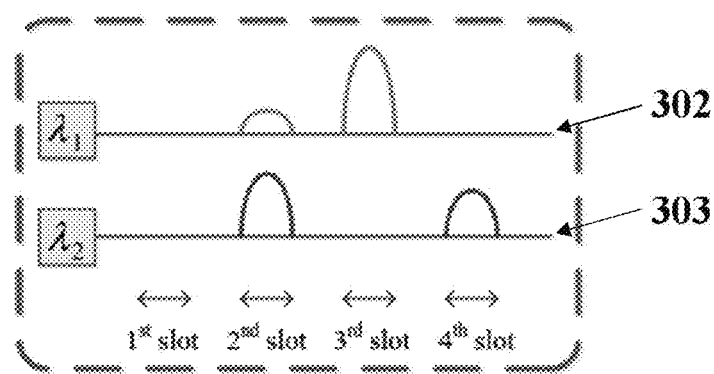
FIG. 3B illustrates an implementation of fluorescence photons detected for a pair of strands within a well in simultaneous paired-end sequencing.
Figure 3C:
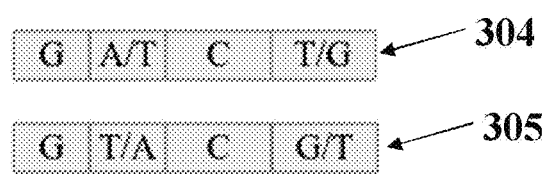
FIG. 3C illustrates a sequences pair generated after simultaneously sequencing a pair of strands within a well.

Referring next to FIGS. 3A-3C, an example of simultaneous sequencing of a pair of strands within each well (second step 102) using a detector with two channels for wavelength filtering is shown. A first well 301 with only one pair of strands 203 including a forward amplified DNA strand 201 and its corresponding pair or reverse strand 202 is shown in FIG. 3A. In one implementation, the sequencing process may be performed for these two strands 203 by detecting fluorescence photons of each oligonucleotide base, illustrated in FIG. 3B.

Each oligonucleotide base—that may be one of {A, C, G, T}—can be linked or associated with a known unique fluorescent tag assignment. The detector can be configured to detect intensities of these fluorescent tags in two different wavelength channels. Because two forward and reverse strands may be sequenced at the same time, intensities of their wavelengths may be detected as $\lambda_1$ for read 302 and $\lambda_2$ for corresponding read-pair 303. However, their associations to the forward and reverse strands may have ambiguities in some cases.

In some implementations, following template preparation, the strands may be understood to be ready for sequencing. In one implementation, each well may include or contain primers bound to the substrate. Thus, as an example, when DNA strands flow in one or more cells, and each time the strands are trapped in a well and react with any primer, DNA polymerases may begin constructing complementary strands quickly. Following this process, the reverse strands may be separated from the forward strands by heating. The procedure may continue until the surface of the well is covered by DNA strands (both forward and reverse strands). It should be noted that, in some cases, the diffusion of DNA strands may be slow relative to the DNA polymerase reactions. In some implementations, only one DNA sample may be located and amplified within a well. Subsequently, sequencing of the forward and the corresponding reverse strands may be conducted at the same time. As noted above, the application of this method can reduce the time required for the sequencing to 50% of the time required by conventional methods, and the consumption of reagents may similarly be halved.

During the sequencing step, fluorescent tagged oligonucleotides may be added to the solution. Each oligonucleotide base has a unique tag, where each of the oligonucleotide bases {A, C, G, T} may be tagged with a unique fluorescent. Thus, in some implementations, the oligonucleotide bases may be distinguished or recognized by the detector by intensity and wavelength. The fluorescent may then be excited at a known wavelength and identified by comparison with a known pattern and a known wavelength. In addition, each nucleotide may be hybridized to the respective complementary oligonucleotide on a DNA strand. After hybridizing an oligonucleotide to a DNA strand, a camera (for example, a PMT camera, CCD cameras, or other such cameras) may be utilized to detect fluorescent tags wavelength and intensity, allowing identification of the corresponding oligonucleotide {A, C, G, T}. Following this step, the fluorescent tags may be cleaved chemically and the solution washed. At the end of each hybridization step, one base of each DNA strand may be detected. This process may continue to sequence a complete read from a DNA strand. In different implementations, read lengths may be about 100-150 bps, while the insert size of paired-end reads may be about 100-1000 bps.

In some implementations, a signal may be detected by utilizing a camera with two different channels, i.e., configured for two different wavelengths. In such cases, the following wavelength and intensity assignment may be considered for each base:

$$\{\lambda_A, \lambda_C, \lambda_G, \lambda_T\} = \{\lambda_{12}, \lambda_1, \ldots, \lambda_2\}$$

where $\lambda_1$ represents a wavelength of oligonucleotide I, I∈{A, C, G, T)}; and $\lambda_{12}$ refers to the assumption that one half of the oligonucleotide bases A will have a first tag with the wavelength $\lambda_1$ and the second half of the oligonucleotide bases A will have a second tag with wavelength $\lambda_2$.

In some implementations, for wavelengths of $\lambda_1$ and $\lambda_2$, Cy5 and Cy3 may be used as fluorescents tagged. In one implementation, no tag may be attached to an oligonucleotide base G. In addition, in some cases, $\lambda_{12}$ refers to half of the oligonucleotide A bases being tagged by Cy3 of wavelength $\lambda_1$ and the other half are tagged by Cy5 of wavelength $\lambda_2$.

As noted with respect to FIG. 1, in third step 103, the association of the reads pairs set may be accomplished by processing the reads pairs set that may be obtained from the second step 102 using the reference genome information. In such cases, a given read and the corresponding read-pair may have known a pre-defined insert size at the template preparation step (first step 101). Thus, using this pre-defined distance, the reads and corresponding read pairs may be located within the reference genome. As a result, the ambiguity of assignment of a given oligonucleotide base may decrease, for example, by extending reads or analyzing all reads that cover a particular base.

In the fourth step 104, a sequences pair including a read sequence and a read-pair sequence may be generated respectively for each pair of reads obtained from second step 102 in order to obtain a sequences pairs set. An example of one sequences pair is shown in FIG. 3C. The example sequences pair includes a read sequence 304 and a read-pair sequence 305 generated from the read 302 and corresponding read-pair 303. In some implementations, it can be understood that some oligonucleotide bases may be uniquely detected while for others, the association may be ambiguous for at least two oligonucleotide bases. If the two oligonucleotide bases are not identical, the association of these bases to forward and reverse stands can be specified to achieve the sequence of the string of oligonucleotides. The associations of the reads pairs set may be determined by mapping the sequences pairs set by Algorithm 1 disclosed further below at TABLE 3, along the reference genome (fifth step 105). In a subsequent step, Algorithm 2, disclosed further below in TABLE 4, may be used for re-sequencing of the mapped sequences pairs set (sixth step 106) in order to obtain the sequence of the string of oligonucleotides.

In some implementations, the process of generating the sequences pairs set may include detecting each pair of oligonucleotide bases along the read and the corresponding read-pair. In these cases, each pair of oligonucleotide bases of the pair of reads may be classified within a subclass of a set of classes that may include a unique class U, a double class D, and a triple class T. The unique class U may include a set of pairs of oligonucleotide bases with a unique possibility for each oligonucleotide base, the double class D may include a set of pairs of oligonucleotide bases with two possibilities for each oligonucleotide base, and the triple class T may include a set of pairs of oligonucleotide bases with three possibilities for each oligonucleotide base.

Furthermore, in some implementations, the process of detecting each pair of oligonucleotide bases along the read and the corresponding read-pair may include scanning all or substantially all of the wells and measuring the intensities of the scanned wells. In some implementations, each well may include a pair of oligonucleotide bases. An example of possible values for these intensities that can be detected by the detector channels are represented below in TABLE 1 and TABLE 2. TABLE 1 corresponds to values for a detector with two channels and TABLE 2 corresponds to values for a detector with four channels.

TABLE 1

The normalized intensities of ($\lambda_1$, $\lambda_2$) using a detector with two channels

| read base | paired base | | | |
|---|---|---|---|---|
| | A | C | G | T |
| A | (1, 1) | (1.5, 0.5) | (0.5, 0.5) | (0.5, 1.5) |
| C | (1.5, 0.5) | (2, —) | (1, —) | (1, 1) |

TABLE 1-continued

The normalized intensities of ($\lambda_1$, $\lambda_2$) using a detector with two channels

| read base | paired base | | | |
|---|---|---|---|---|
| | A | C | G | T |
| G | (0.5, 0.5) | (1, —) | (—, —) | (—, 1) |
| T | (0.5, 1.5) | (1, 1) | (—, 1) | (—, 2) |

TABLE 2

The normalized intensities of ($\lambda_1$, $\lambda_2$, $\lambda_3$, $\lambda_4$) using a detector with four channels

| read base | paired base | | | |
|---|---|---|---|---|
| | A | C | G | T |
| A | (2, 0, 0, 0) | (1, 1, 0, 0) | (1, 0, 1, 0) | (1, 0, 0, 1) |
| C | (1, 1, 0, 0) | (0, 2, 0, 0) | (0, 1, 1, 0) | (0, 1, 0, 1) |
| G | (1, 0, 1, 0) | (0, 1, 1, 0) | (0, 0, 2, 0) | (0, 0, 1, 1) |
| T | (1, 0, 0, 1) | (0, 1, 0, 1) | (0, 0, 1, 1) | (0, 0, 0, 2) |

In some implementations, a pair of oligonucleotide bases (b, b*) including an oligonucleotide base b of a read and a corresponding base b* within the read-pair read may be detected using a detector with two channels for sequencing. In such a case, the pair can be detected in one of the classes including: the unique class U represented by (b, b*)∈U{(C, C), (G, G), (T, T)}, the double class D represented by (b, b*)∈D{(A, C), (C, A), (A, G), (G, A), (A, T), (T, A), (C, G), (G, C), (G, T), (T, G)}, and the triple class T represented by (b, b*)∈T{(A, A), (C, T), (T, C)}. If the pair of oligonucleotide bases (b, b*) is located in the unique class U, both b and b* may be decoded uniquely by their tags. If the (b, b*) is located in the double class D or the triple class T, the detected b and b* is associated between the read and the read-pair. Thus, if one of b or b* is resolved by fifth step 105 and sixth step 106, the other base can be determined uniquely.

As a non-limiting example, using reads and reads-pairs with a length L of about L=100 or L=150 pair of oligonucleotide bases (bps) from a chr19 of a human genome hg19 and a pre-determined value for insert size of about 100 oligonucleotide bases to more than about 1000 oligonucleotide bases, only a small fraction of detected sequences may be mapped to more than two possible locations, and most of detected sequences may be mapped uniquely to the reference genome. If the size of U becomes larger, mapping (fifth step 105) a sequences pairs set along the reference genome becomes simpler with more precision. However, in cases where oligonucleotide bases are of the two other classes (D or T) it may be helpful to find the original location of each sequences pair. Thus, outputs of the fourth step 104 may include a sequences pairs set of oligonucleotide bases of length L such that each oligonucleotide base may be associated with one of three classes (unique, double, and triple).

Furthermore, in some implementations, at the fifth step 105, the sequences pairs set generated in the fourth step 104 may be mapped along the reference genome within the pre-defined insert size. In some implementations, the sequences pairs set may be mapped along the reference genome. The mapping can occur via a procedure including: (1) searching for each sequences pair of the sequences pairs set along the reference genome by analyzing the oligonucleotide bases of the sequences pair that may be classified in the unique class, in order to locate the read sequence and the read-pair sequence of the searched sequences pair along the reference genome; (2) aligning the located sequences pair along the reference genome if the read sequence and the read-pair sequence have a distance from each other equal to the pre-defined insert size distance; and/or (3) accepting the aligned sequences pair along the reference genome if the oligonucleotide bases of the sequences pair that are classified in the double class or the triple class are consistent with corresponding oligonucleotide bases of the reference genome.

may include a pair of substrings that may be placed within a distance of D±Δ along the reference genome. Between the accepted substrings for each $r_i$, those pairs of substrings may be chosen such that the other oligonucleotide bases may be consistent with corresponding oligonucleotide bases of $r_i$ at locations shown by D ($r_i$) and T ($r_i$). Furthermore, within an $r_i$, the substrings may differ with oligonucleotide bases of D (r) and T (r) at most at two oligonucleotide bases to handle sequencing errors and variations between the reference genome and the string of oligonucleotides.

TABLE 3

A procedure for mapping the sequences pairs set along the reference genome
Algorithm 1

Input:
N reads of length $L_i$ of a target genome with G bases plus a reference genome with the same length.
Output:
S($r_i$)'s: List of strings and their locations on the reference genome for the $i^{th}$ read, i ∈ {1, ... , N}.
Initiation:
1:  for i = 1 to N do
2:     Determine U($r_i$), D($r_i$) and T($r_i$) for the $i^{th}$ read $r_i$.
3:  end for
4:  Set S = ∅
1:  for i = 1 to N do
2:     Generate $\hat{r}_i$ by keeping only bases of U($r_i$) and set other bases to be N.
3:  end for
4:  Call BWT for all $\hat{r}_i$.
5:  for i = 1 to N do
6:     Sort reports of $\hat{r}_i$ by their positions and save them in S. The position of the $m^{th}$ report in S is $l_{S(m)}$.
7:     for j = 1 to |S| do
8:        for k = j + 1 to |S| do
9:           if $l_{S(k)} - l_{S(j)} > D + \Delta$ then
10:             Break.
11:          else
12:             if $l_{S(k)} - l_{S(j)} \geq D - \Delta$ then
13:                Set E to be Hamming distance of S(j) and $r_i$ in D($r_i$) and T($r_i$) locations.
14:                if E ≤ 2 then
15:                   Add {(S(j), $l_{S(j)}$), (S(k), $l_{S(k)}$)} to S($r_i$).
16:                end if
17:             end if
18:          end if
19:       end for
20:    end for
21: end for In addition, after generating the sequences pairs set for the set of pairs of reads in the fourth step 104, the sequences pairs set may be mapped on the reference genome within the predefined insert size represented by D±Δ, where D refers to an average of the pre-defined insert size distance and Δ refers to a variance of the pre-defined insert size distance.

In one implementation, Algorithm 1 shown below in TABLE 3 may be executed or used to map the output sequences pairs set from the fourth step 104. Algorithm 1 includes a procedure for generating the sequences pairs set and mapping the sequences pairs set along the reference genome. In such cases, each sequences pair $r_i$ with classes U ($r_i$), D ($r_i$) and T ($r_i$) may be considered, identified, or analyzed. Each n may be searched on the reference genome by taking into consideration only bases of U ($r_i$) and disregarding other bases. For this purpose, a new sequence $\hat{r}_i$ may be generated from a given $r_i$ by retaining bases of U (r) and disposing or positioning ambiguous character N at locations that D (r) and T (r) may specify. As a result, the $\hat{r}_i$ may be aligned to the reference genome by using an algorithm based on the Burrows-Wheeler Transform (BWT). Finally, all $\hat{r}_i$ is aligned to the reference genome may be accepted, such that the aligned $\hat{r}_i$ by the algorithm In sixth step 106, the mapped sequences pairs set of fifth step 105 may be re-sequenced to obtain the sequence of the string of oligonucleotides. For a sequences pair, some oligonucleotide bases may be resolved by mapping to the reference genome (fifth step 105), for example, by the provided mapping Algorithm 1, while other oligonucleotide bases can be resolved by using information of other reads in the re-sequencing step (sixth step 106). Re-sequencing the mapped sequences pairs set may include denoting oligonucleotide bases of the mapped sequences pairs set. In such a case, a set of oligonucleotide bases are denoted within the mapped read sequences of the mapped sequences pairs set that are aligned to a first oligonucleotide base of the reference genome as a first set of c-bases. Furthermore, a set of oligonucleotide bases are denoted within the mapped read-pair sequences of the mapped sequences pairs set that are aligned to a second oligonucleotide base of the reference genome as a first set of cp-bases. This can be followed by assigning a first subset of the first set of c-bases to the first oligonucleotide base of the reference genome and a second subset of the first set of cp-bases to the second oligonucleotide base of the reference genome. At this time, the sequence of the string of oligonucleotides can be determined.

In this example, the first subset can include the most probable oligonucleotide bases of the first set of c-bases, and the second subset can include the most probable oligonucleotide bases of the first set of cp-bases. For purposes of this description, the most probable oligonucleotide bases can be understood to have a maximum vote among the unique class U, the double class D, and the triple class T for an oligonucleotide base of the first set of c-bases or the first set of cp-bases. In one implementation, determining the sequence of the string of oligonucleotides may include setting a first oligonucleotide base of the string of oligonucleotides equal to the first oligonucleotide base and a second oligonucleotide base of the string of oligonucleotides equal to the second oligonucleotide base, if the list of the most probable oligonucleotide bases of the c-bases is uniquely assigned to the first oligonucleotide base of the reference genome, or if the list of the most probable oligonucleotide bases of the cp-bases may be uniquely assigned to the second oligonucleotide base of the reference genome.

Furthermore, in some implementations, re-sequencing of the mapped sequences pairs set may be conducted using a procedure that can be represented by Algorithm 2 shown below in TABLE 4.

TABLE 4

A procedure for re-sequencing the mapped sequences pairs set
Algorithm 2

Input:
N sequences of length $L_i$ of a string of oligo-nucleotides with G bases plus a reference genome with the same length. $U_{assign}$ option for assigning of all non-unique bases of target genome.
Output:
A re-sequenced target genome.
Initiate:
1:   for g = 1 to G do
2:      $V_g = \emptyset$
3:   end for
4:   U = 0, $U_{old}$ = 0 and imp = TRUE.
1:   while U < G and imp = TRUE do
2:      for g = 1 to G do
3:         Set $R_g$ equal to all c-bases of the $g^{th}$ base of the reference genome up to this step.
4:         Set $R_g^*$ equal to all cp-bases of the $g^{th}$ base of the reference genome up to this step.
5:         Set $V_g$ to the maximum vote bases between $R_g$.
6:         if $|V_g|$ = 1 then
7:            U = U + 1.
8:         else
9:            for h = 1 to $|R_g^*|$ do
10:              Set $b_h$ to the $h^{th}$ base of $R_a^*$.
11:              if $|V_{b_h}|$ = 1 then
12:                 Update V by considering $h^{th}$ base of $R_g$ and remove $V_{b_h}$ from its possible bases.
13:                 U = U + 1.
14:                 Break.
15:              end if
16:           end for
17:        end if
18:     end for
19:     if U = $U_{old}$ then
20:        imp = FALSE.
21:     else
22:        $U_{old}$ = U.
23:     end if
24:  end while
25:  if $U_{assign}$ = TRUE then
26:     for g = 1 to G do
27:        $V_{max}$ = 0.
28:        for h = 1 to $|V_g|$ do
29:           Let $R_h$ is number of cp-reads for $v_h \in V_g$.
30:           if $n_h > V_{max}$ then
31:              Set $V_{max} = R_h$.
32:           end if
33:        end for
34:        for h = 1 to $|V_g|$ do
35:           if $n_h < 0.8 \times V_{max}$ then
36:              Remove $v_h$ from $V_g$.
37:           end if
38:        end for
39:        Assign $V_g$ to the $g^{th}$ base of the reference genome.
40:     end for
41:  end if In Algorithm 2 above, for the $g^{th}$ oligonucleotide base of reference genome, all c-bases of the $g^{th}$ oligonucleotide base may be set in $R_g$. The most probable oligonucleotide base from {A, C, G, T} may be found by using a maximum vote between oligonucleotide bases of $R_g$. For all possible oligonucleotide bases of unique, double, and triple oligonucleotide bases of $R_g$, the same weight may be used in voting. A list $V_g$ of most probable oligonucleotide bases may be assigned to the $g^{th}$ oligonucleotide base and this procedure may be continued for the next oligonucleotide base within the reference genome. After scanning all oligonucleotide bases of the reference genome, in some implementations, the procedure may return and started from the first oligonucleotide base again. If any oligonucleotide base is uniquely resolved, the procedure may be continued with the next oligonucleotide base. Otherwise, if any cp-base of a given oligonucleotide base b is uniquely resolved at the previous step, then the oligonucleotide base b is also determined. Thus, the process of Algorithm 2 may end or be terminated when all oligonucleotide bases are uniquely resolved/re-sequenced or the remaining oligonucleotide bases cannot be resolved/re-sequenced.

In some implementations, the above-described process may be performed by scanning all oligonucleotide bases of the reference genome. In this method, all oligonucleotide bases may be specified by a maximum vote method between all aligned/mapped read sequences. Specifying any oligonucleotide base may help to determine corresponding bases within read-pair sequences. By running this procedure iteratively, most or all oligonucleotide bases of the string of oligonucleotides may be re-sequenced.

Furthermore, for a given oligonucleotide base g along the reference genome, all mapped sequences aligned to this oligonucleotide base may be considered or examined. In some implementations, $R_g$ may be set as equal to all c-bases and $R_g^*$ may be set as equal to all cp-bases of the oligonucleotide base. In addition, $V_g$ may be associated with a list of maximum repeated oligonucleotide bases within $R_g$. If $V_g$ has one member, oligonucleotide base g may be called/re-sequenced as that single oligonucleotide base. Otherwise, all possible oligonucleotide bases within read-pair sequences (in $R_g^*$) are considered. If any of these oligonucleotide bases has one (maximum) repeated oligonucleotide base (by using the maximum vote method), then this oligonucleotide base may be removed from $V_g$. This procedure may continue for all oligonucleotide bases within the reference genome iteratively. In addition, any update in $V_g$ also updates that of $V_h$, where h includes associated oligonucleotide bases with oligonucleotide base g by read sequences and the corresponding read-pair sequences. If no updates occur between the members of $V_g$, $V_g$ may be assigned to the oligonucleotide base g for all oligonucleotide bases within the reference genome. A more specific re-sequencing for an oligonucleotide base g can occur by a removal of the base from list $V_g$, if the oligonucleotide bases within $V_g$ for the corresponding number of cp-reads is lower than 0.8 of the maximum number of cp-reads between all bases of $V_g$.

Figure 4:
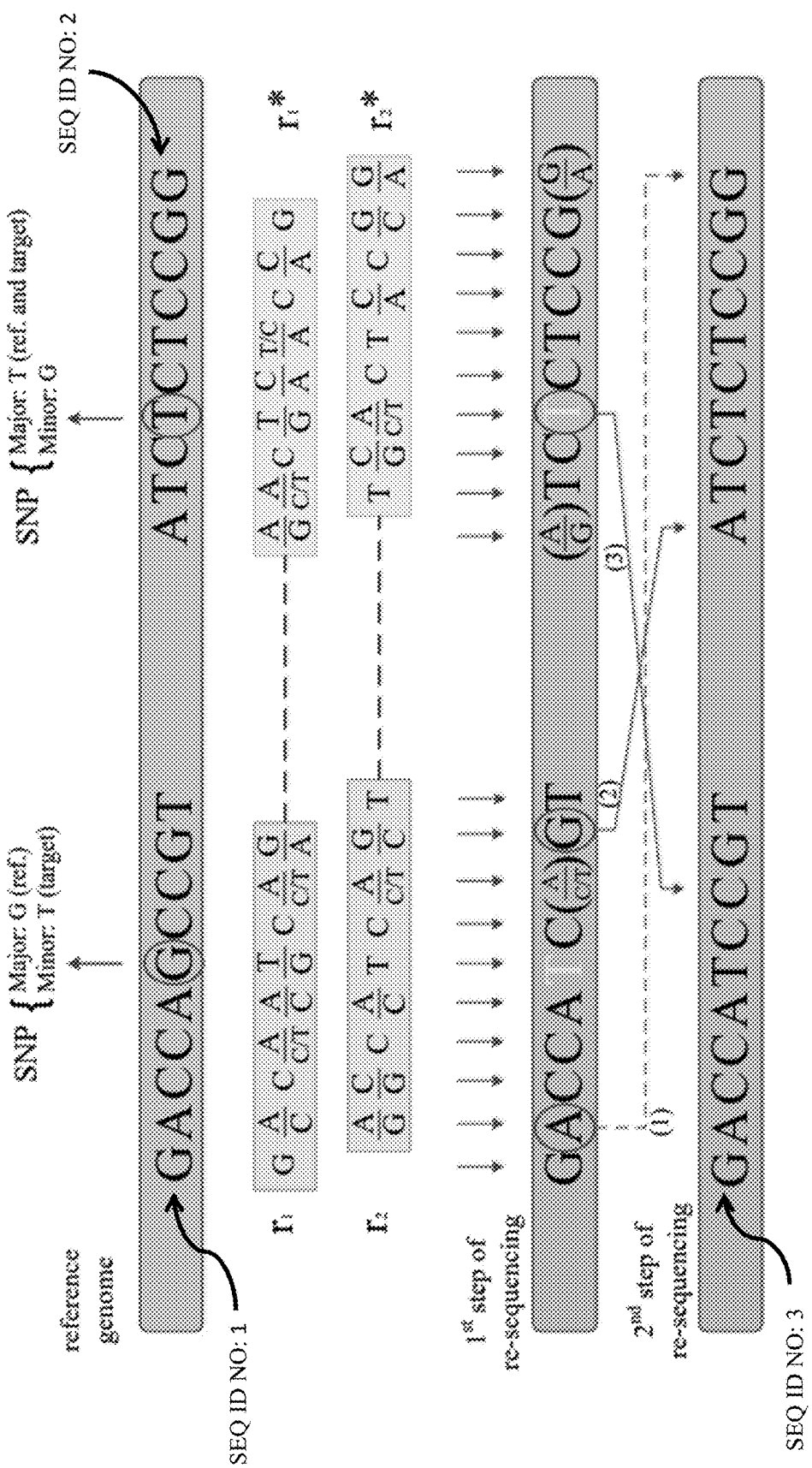
FIG. 4 illustrates a schematic of an implementation of the re-sequencing procedure.

Referring now to FIG. 4, details of an implementation of the re-sequencing algorithm are provided. As illustrated in FIG. 4, read sequence (r) and read-pair sequence (r*) may be anchored to the reference genome by their unique oligonucleotide bases, and uncertain or indeterminate oligonucleotide bases with two options. In the example of FIG. 4, three oligonucleotide bases of read $r_1$ and the corresponding pair $r_1^*$ are unique, while six uncertain oligonucleotide bases within $r_1$ and $r_1^*$ exist. Similarly, in this example, four oligonucleotide bases of read $r_2$ and the corresponding pair $r_2^*$ are unique, while five oligonucleotide bases within $r_2$ and $r_2^*$ exist. Some indeterminate oligonucleotide bases have three possible options when (C, T) or (A. A) bases are located in two sequences in the same step of the reading process. When a Single Nucleotide Polymorphism (SNP) exists within target genome, the provided algorithm detects the SNP by application of all other reads which cover the SNP as well as their pairs to correctly re-sequence the target genome. It should be understood that FIG. 4 is shown as an illustration of an optimal re-sequencing process, with two reads following the two steps of the provided algorithm.

Thus, one important aspect of DNA re-sequencing is SNA detection. It is desirable to detect SNP loci and distinguish these bases for a target genome. In order to resolve SNP loci, an alignment algorithm can be utilized, such as Algorithm 1, to handle mismatches. Following the alignment stage, SNPs can be resolved in the re-sequencing stage. If any corresponding base in the re-sequenced reads and the corresponding pairs of a given SNP base is resolved then a SNP base can also be resolved. Otherwise, if all corresponding bases in the re-sequenced reads and the corresponding pairs stay unresolved, an SNP may remain unresolved.

DNA/RNA Haired-End Sequencing

In one implementation of a paired-end sequencing method, DNA/RNA fragments from an individual may be immobilized or disposed stationary on a surface. These fragments may be prepared by library preparation techniques in which each fragment may have an approximately known length. Once a fragment diffuses to a well, the DNA polymerase can amplify the fragment within the well. However, after the amplification step, some copied fragments may be in the forward direction and some may be in the reverse direction. As disclosed herein, both of these amplified fragments can be sequenced simultaneously by the disclosed methods. Thus, reads and paired reads may be extracted from both sides of these fragments. Furthermore, the mapping and re-sequencing steps, using the reference genome, may be accomplished by either the provided method for DNA reads and their pairs, or using transcriptome for RNA reads and their pairs.

Targeted Sequencing

A number of genomic applications rely on the sequencing of targeted locations on the genome. In one implementation, the applications can involve N target regions where fragments of each region may be synthesized by one of two specific primers randomly. As a result, the surface of the wells that are distributed over the template may be covered with two kind of primers and their corresponding reverse, complementary sequences. In such a case, more than one primer may appear in each well. Following the amplification step, each well may contain up to two DNA sequences. Thus, the steps of sequencing, mapping and re-sequencing inside each well—containing at most two different DNA sequences—may be accomplished by the disclosed method. For purposes of clarity, some examples are provided herein below.

EXAMPLE 1

Classification of Three Possible Classes for Sequenced Oligonucleotides

Figure 5A:
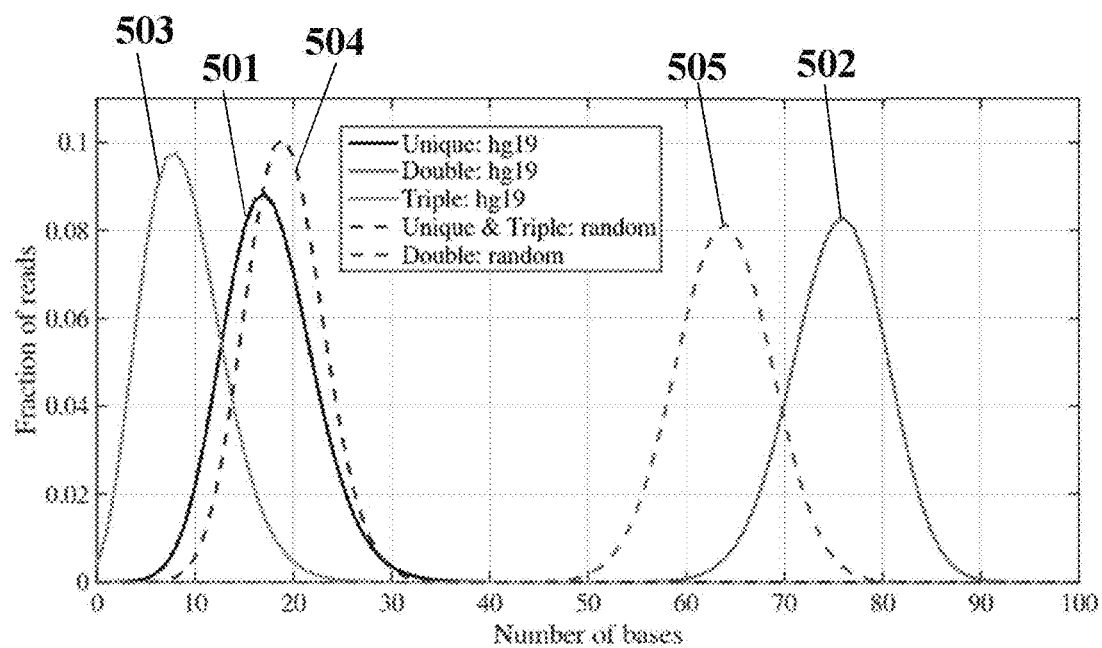
FIG. 5A illustrates an implementation of a fraction of a sequences pairs set of human genome hg19 with a length of L=100 bps and a number of oligonucleotide bases in each three classes of U, D, and T.
Figure 5B:
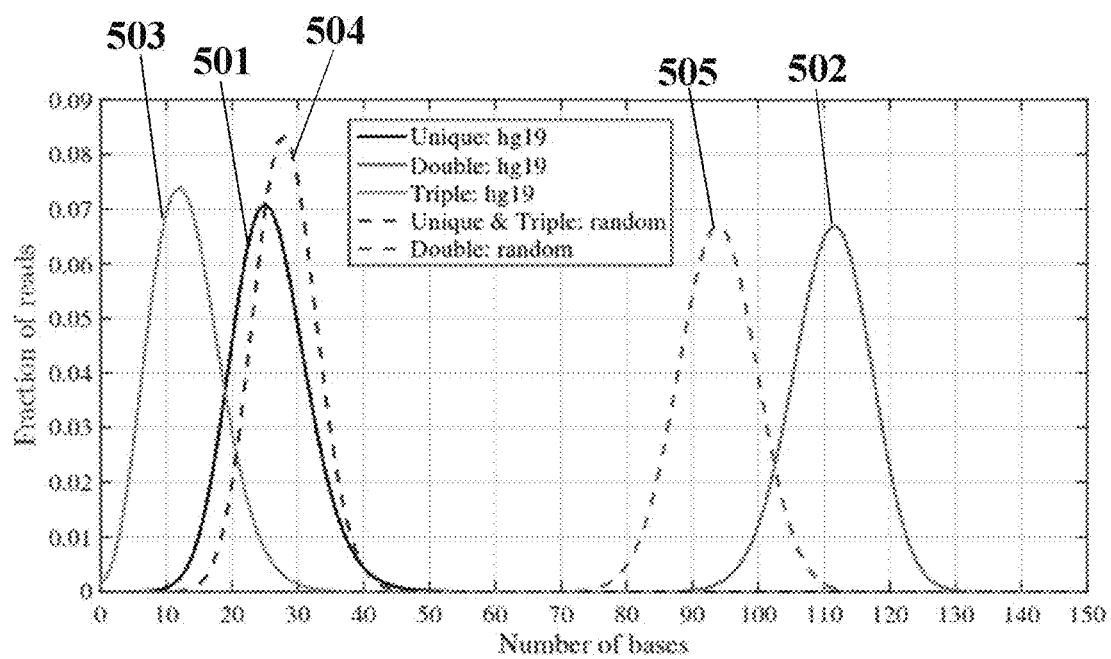
FIG. 5B illustrates an implementation of a fraction of a sequences pairs set of human genome hg19 with a length of L=150 bps and a number of oligonucleotide bases in each three classes of U, D, and T.

To find a number of each class of oligonucleotide bases within read sequences in a human genome hg19, insert sizes of D={400, 500, 700} and read lengths of L={100, 150} were considered and examined. Error-less read sequences and their read-pairs were generated from each oligonucleotide base of human genome hg19. For each read sequence, a number of each of the base classes was determined, including the unique, double, and triple classes. Results for different read lengths L=100 and L=150 with D=500 are shown in FIGS. 5A and 5B. It should be understood that by changing the insert size, the same results may be achieved. In addition, FIGS. 5A and 5B show a number of elements of all classes for a random genome (in this example, IID genome).

FIGS. 5A and 5B show fractions of the sequences pairs set with a number of oligonucleotide bases in each of the three classes. Noiseless sequences were generated from each oligonucleotide base of human genome hg19 with two lengths of L=100 bps (FIG. 5A) and L=150 bps (FIG. 5B).

An oligonucleotide base b within a read sequence and its corresponding oligonucleotide base b* within the read-pair sequence were categorized into three classes (b, b*∈{A, C, G, T}), including (1) a Unique class 501, with all pairs of(b, b*) with b=b* and b≠A; (2) a Double class 502, with all pairs of (b, b*) where b≠b* and (b, b*)∈/{(C, T), (T, C)}; and (3) a triple class 503, with (b, b*)∈{(C, T), (T, C), (A, A)}. In addition, for comparison of human results with a random genome, FIGS. 5A and 5B illustrate substantially similar results when a random reference genome is used, as shown by the first curve 504 for the unique and triple classes and the second curve 505 for the double class in each figure.

However, it should be understood that a number of elements of the triple class in the human genome do not represent random behavior. Thus, this class of bases (i.e., {(C, A), (T, G), (A, T)} pairs on the forward stand) may be associated with important information for the human genome. For example, approximately 99% of read sequences of length L=100 have more than 8 unique oligonucleotide bases, and approximately 99% of read sequences of L=150 have more than 14 unique oligonucleotide bases. It should be noted that these numbers may double when each read sequence with the corresponding pair is examined. In addition, approximately 99% of read sequences of length L=100 have more than 64 double oligonucleotide bases and approximately 99% of read sequences of L=150 have more than 96 double oligonucleotide bases.

EXAMPLE 2

Manning for Human Genome hg19

In this example, a simulation for alignment chr19 of human genome hg19 was run and is described herein. In this case, $N=10^6$ paired-end read sequences were generated of lengths L={100, 150} bps and error rates of ε={0, 1}% from the hg19 genome. Only mismatch error models and insert sizes of D±Δ=500±10 bps were considered. As the sequences pairs set were extracted randomly from the chr19, it can be understood that the effects of A may be discarded. Thus, Δ=0 was assumed. A sequence was generated based on the provided detection stage for each read and its read-pair. The genome was then searched for these sequences. Error-less reads, including all sequences that were correctly aligned to the genome such that 99.43% of sequences of length L=100 bps and 99.52% of sequences of length L=150 bps, were uniquely mapped.

Figure 6:
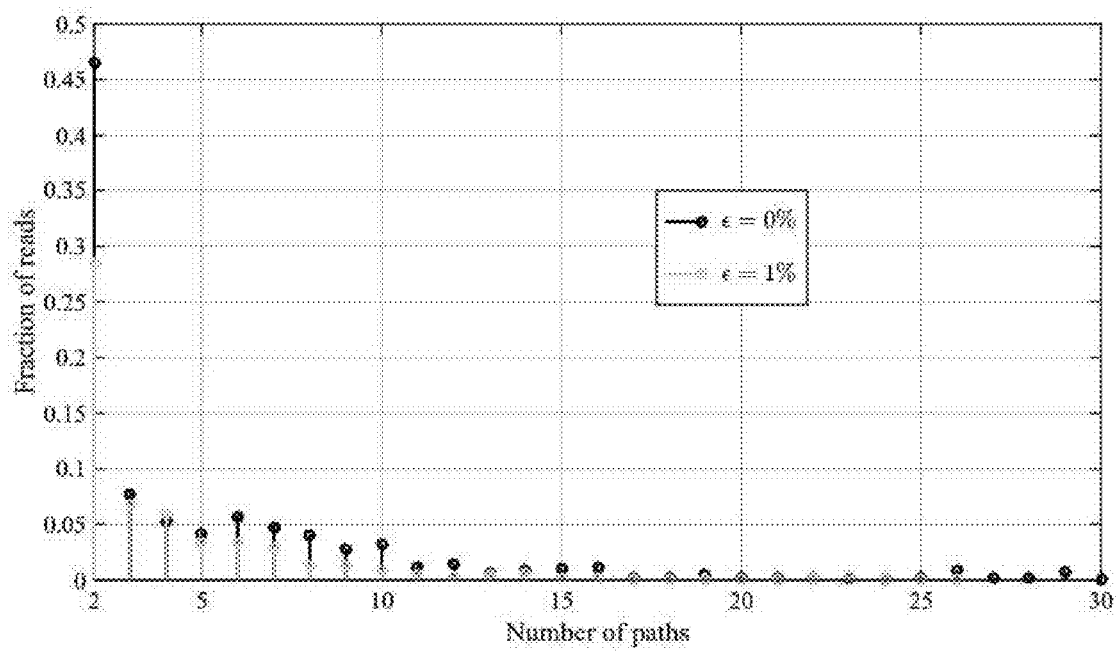
FIG. 6 illustrates an implementation of a number of reported paths for multiple mapped, decoded, and generated sequences with a length 100 bps.

A number of the reported locations for multiple mapped sequences are illustrated in FIG. 6. FIG. 6 shows a number of the reported paths for multiple mapped decoded and generated sequences of length 100 bps. In this simulation, $N=10^6$ paired-end reads with an insert size of 500 bps and error rates of {0, 1}% were generated from chr19 of human genome hg19. Based on detection stage output, one sequence for each read and its pair was generated. These reads were aligned to the genome with a maximum Hamming distance of {0, 4} for error rates of {0, 1}%, respectively. In this example, approximately 99.43% of these sequences for error rates of 0% and about 99.05% of these sequences for error rates of 1% were aligned uniquely to the genome.

Figure 7:
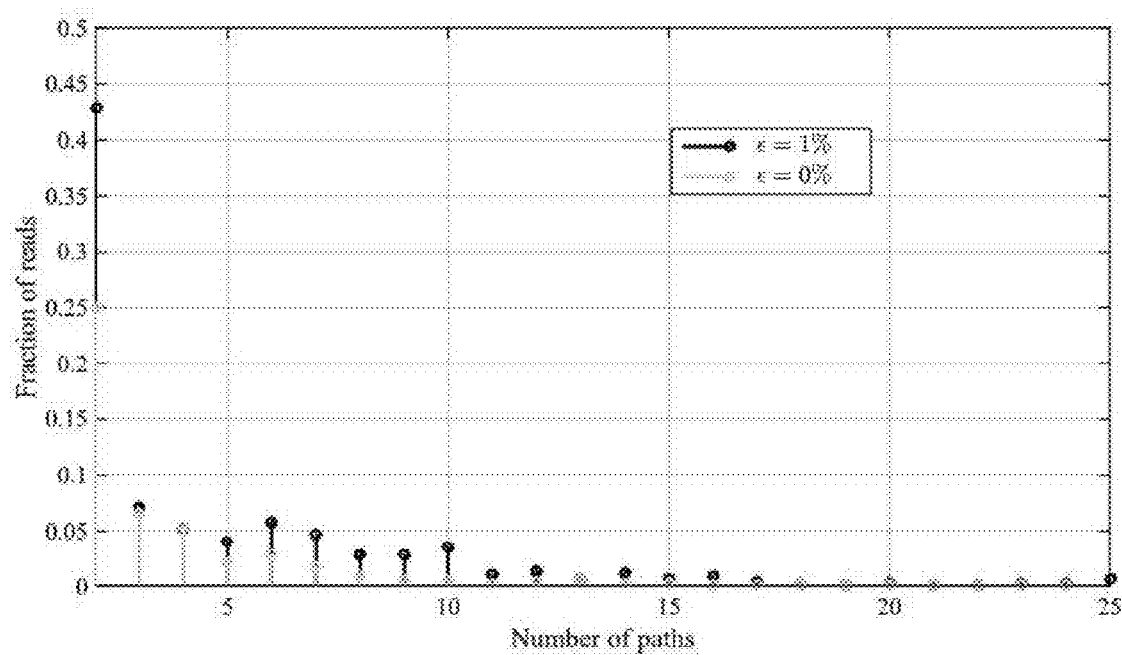
FIG. 7 illustrates an implementation of a number of reported paths for multiple mapped, decoded, and generated sequences with a length 150 bps.

Furthermore, to simulate noise in reads, mismatch errors with a rate of 1% were added to all read sequences and read-pairs by a random model (here, an IID model). A sequence was constructed from each noise augmented read and its read-pair that was consistent with the detection stage described herein. In this case, almost all sequences were correctly aligned to the genome such that approximately 99.05% of sequences of length L=100 bps and 99.12% of sequences of length L=150 bps were uniquely mapped. In addition, a number of reported locations for multiple mapped sequences in the presence of noise are illustrated in FIG. 7. Therefore, the alignment method may be optimized, as most of reads were aligned correctly and uniquely to their correct location.

FIG. 7 presents a number of reported paths for multiple mapped decoded and generated sequences of length 150 bps. In this simulation, $N=10^6$ paired-end reads with an insert size of 500 bps and error rates of {0, 1}% were generated from chr19 of human genome hg19. Based on the output of the detection stage, one sequence for each read and its read-pair was generated.

These sequences were aligned to the genome with a maximum Hamming distance of {0, 6} for error rates of {0, 1}%, respectively. Approximately 99.52% of these sequences for error rate of 0% and approximately 99.15% of these sequences with an error rate of 1% were aligned uniquely to the genome.

EXAMPLE 3

Re-sequencing for Human Genome hg19

In this example, re-sequencing was simulated for human genome hg19. Error-less paired-end reads of lengths L={100, 150} bps and insert sizes of D={400, 500, 700} bps were generated from each base of the genome, where N L={0.5, 0.75, 1}×G log G. It should be noted that number of reads N and read length L must satisfy N L≥G log G, as an approximation of the re-sequenced coverage bound. It was further assumed in this simulation that all reads were mapped correctly to their locations. Results of this simulation for calling/re-sequencing using Algorithm 2 for D=500 and L={100, 150} bps are presented below in TABLE 5. For other values of D, it can be understood that the results may be the same as for D=500. In all cases, after the third step of the provided algorithm, no oligonucleotide base remained unresolved.

TABLE 1

The number of the unresolved (not uniquely decoded) bases of the reference genome using the provided re-sequencing algorithm for human genome hg19, and read length of l = {100, 150} bps and insert size of d = 500

| | Depth | | | | | |
|---|---|---|---|---|---|---|
| | c = 0.5 log G | | c = 0.75 log G | | c = log G | |
| Read length | 1$^{st}$ step | 2$^{nd}$ step | 1$^{st}$ step | 2$^{nd}$ step | 1$^{st}$ step | 2$^{nd}$ step |
| L = 100 | 2.04% | 1E−5 | 0.52% | 7E−6 | 0.15% | 4E−6 |
| L = 150 | 2.63% | 2E−5 | 1.01% | 1E−5 | 0.19% | 5E−6 |

The results of the human genome in TABLE 5 show that by using an insert size of 500 bps, a read length of L=150 bps, and a depth of reads c≥0.5 log G, most bases of the genome were resolved.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A paired-end sequencing method for sequencing a string of oligonucleotides, the method comprising:

preparing a template comprising a plurality of wells, each well containing a pair of strands from the string of oligonucleotides, the pair of strands comprising a forward strand and a corresponding reverse strand;

generating a reads pairs set comprising a plurality of reads pairs by simultaneously sequencing the pair of strands within each well, each reads pair comprising a read associated with the forward strand of the well and a corresponding read-pair associated with the reverse strand of the well, comprising simultaneously detecting fluorescence intensities of each nucleotide base of the forward strand and corresponding nucleotide base of the reverse strand, wherein the read and the corresponding read-pair have a pre-defined insert size distance in a range between 100 nucleotide bases and 1000 nucleotide bases from one another along the string of oligonucleotides; and processing the reads pairs set, comprising:
generating a sequences pairs set comprising a plurality of sequences pair by classifying and detecting nucleotide bases possibilities for each corresponding pair of nucleotide bases within a read and a corresponding read-pair of the reads pairs set based on the detected fluorescence intensities, each sequences pair comprising a read sequence and a read-pair sequence corresponding to a reads pair of the reads pairs set;

mapping the sequences pairs set along a reference genome, comprising:
locating the sequences pairs set along the reference genome by locating each classified and detected sequences pair of the sequences pairs set along the reference genome;

aligning the located sequences pair set by aligning each located sequences pair of the located sequences pair set along the reference genome responsive to read sequence and read-pair sequence of the located sequences pair having a distance from each other equal to the pre-defined insert size distance along the reference genome; and accepting each aligned sequences pair of the aligned sequences pair set along the reference genome responsive to nucleotide bases of the aligned sequences pair being consistent with corresponding nucleotide bases of the reference genome; and obtaining a sequence of the string of oligonucleotides by iteratively re-sequencing the mapped sequences pairs set, wherein the re-sequencing the mapped sequences pairs set comprises determining not accepted nucleotide bases of each aligned sequences pair of the aligned sequences pair set based on nucleotide bases of accepted sequences pairs of the aligned sequences pair set.

2. The method of claim 1, wherein preparing the template comprises:

obtaining a plurality of strands by shearing a number of copies of the string of oligonucleotides;

placing the plurality of strands within the plurality of wells of the template by immobilizing the plurality of strands on the template, each well of the plurality of wells containing a strand of the plurality of strands;

obtaining the forward strand and the corresponding reverse strand coupled to each other within each well of the plurality of wells by amplifying each strand placed in each well of the plurality of wells using at least one of a cloning based technique or a free-cloning based technique; and obtaining the pair of strands within each well by separating each forward strand from its corresponding reverse strand within each well by denaturing process.

3. The method of claim 1, wherein generating the reads pairs set comprising the plurality of reads pairs by simultaneously sequencing the pair of strands within each well comprises:

hybridizing fluorescent tagged nucleotides to the forward strand and the corresponding reverse strand in each well by adding fluorescent tagged nucleotides to the template; and detecting fluorescence intensity of hybridized nucleotide bases along the forward strand and the corresponding reverse strand simultaneously in each well for at least 50 respective pair nucleotide bases of the forward strand and the corresponding reverse strand using a detector with at least two channels for wavelength filtering in order to obtain the reads pairs set.

4. The method of claim 3, wherein the detector comprises at least one of two channels for wavelength filtering or four channels for wavelength filtering.

5. The method of claim 1, wherein generating the sequences pairs set comprises:

classifying each pair of nucleotide bases of each reads pair within one of three classes, the three classes comprising:

a unique class U, comprising a set of pairs of nucleotide bases with a unique possibility for each nucleotide base;

a double class D, comprising a set of pairs of nucleotide bases with two possibilities for each nucleotide base; and a triple class T, comprising a set of pairs of nucleotide bases with three possibilities for each nucleotide base; and detecting each pair of nucleotide bases along both the read and the corresponding read-pair of each reads pair within one of the three classes based on the detected fluorescence intensities.

6. The method of claim 5, wherein mapping the sequences pairs set along the reference genome comprises:
   searching for each sequences pair of the sequences pairs set along the reference genome by considering oligonucleotide bases of the sequences pair that are classified in the unique class U;
   locating the read sequence and read-pair sequence of the searched sequences pair along the reference genome by retaining nucleotide bases of the searched sequences pair that are classified the unique class U and positioning an ambiguous character N at nucleotide bases of the searched sequences pair that are classified in at least one of the double class D or triple class T;
   aligning the located sequences pair along the reference genome if the read sequence and the read-pair sequence are associated with a distance substantially equal to the pre-defined insert size distance by associating nucleotide bases of the located sequences pair to corresponding nucleotide bases of the reference genome using a procedure based on Burrows-Wheeler Transform (BWT) procedure; and
   accepting the aligned sequences pair along the reference genome if nucleotide bases of the aligned sequences pair that are classified in one of the double class D or the triple class T are consistent with corresponding nucleotide bases of the reference genome.

7. The method of claim 6, wherein generating the sequences pairs set and mapping the sequences pairs set along the reference genome is carried out using a procedure, the procedure comprising:
   classifying nucleotide bases possibilities for each corresponding pair of nucleotide bases within a read and a corresponding read-pair of the reads pairs set by determining three sets for each sequences pair $r_i$ and $r_i^*$ from the sequences pairs set r $\{r_1, r_2, \ldots, r_i, \ldots, r_N, r_1^*, \ldots, r_N^*\}$, the three sets comprising the unique class $U_{(ri)}$, the double class $D_{(ri)}$ and the triple class $T_{(ri)}$;
   initializing a set S $\{S_{(r1)}, S_{(r2)}, \ldots, S_{(ri)}, S_{(rN)}\}$ equal to zero (Ø), wherein $S_{(ri)}$ comprises the mapped sequences pairs set that comprises a set of strings and corresponding locations on the reference genome for each read sequence $r_i$;
   searching for each sequences pair of the sequences pairs set along the reference genome and locating the read sequence and read-pair sequence of the searched sequences pair along the reference genome by generating a set $\hat{r}\{\hat{r}_1, \ldots, \hat{r}_i, \ldots, \hat{r}_N\}$ respective to the set r by retaining the set U $(r_i)$ and setting other nucleotide bases as N;
   aligning the located sequences pair along the reference genome by aligning the set $\hat{r}$ to the reference genome using an algorithm based on a Burrows-Wheeler Transform (BWT) to find the mapped sequences pairs set for $r_i$; and
   updating the set S by updating each $S_{(ri)}$, comprising:
      sorting and saving the mapped sequences pairs set for each $r_i$ as $S_{(ri)}$, wherein the location of a $m^{th}$ string is represented by $l_{S(m)}$, and m is within a set of $\{1, \ldots, m, \ldots, |S|\}$ and $|S|$ the size of $S_{(ri)}$; and
      accepting the aligned sequences pair along the reference genome responsive to nucleotide bases of the aligned sequences pair that are classified in one of the double class D or the triple class T being consistent with corresponding nucleotide bases of the reference genome, comprising:
         setting a parameter E to be equal to a Hamming distance of each S(j) and $r_i$ in $D(r_i)$ and $T(r_i)$ locations if the distance between a $l_{S(j)}$ and the next $l_{S(k)}$ is $\geq D-\Delta$, wherein j is within $\{1, \ldots, |S|\}$, k is within $\{j+1, \ldots |S|\}$, D represents an average of the pre-defined insert size distance, and $\Delta$ represents a variance of the pre-defined insert size distance; and
         adding $\{(S_{(j)}, l_{S(j)}), (S_{(k)}, l_{S(k)})\}$ to $S_{(ri)}$ if E≤2, wherein updating the $S_{(ri)}$ ceases if the distance between a $l_{S(j)}$ and next $l_{S(k)}$ is $>D+\Delta$.

8. The method of claim 1, wherein obtaining the sequence of the string of oligonucleotides by iteratively re-sequencing the mapped sequences pairs set comprises: denoting nucleotide bases of the mapped sequences pairs set, the denoting comprising:
   denoting a set of nucleotide bases within the mapped read sequences of the mapped sequences pairs set that are aligned to a $g^{th}$ nucleotide base of the reference genome as a first set of c-bases; and
   denoting a set of nucleotide bases within the mapped read-pair sequences of the mapped sequences pairs set that are aligned to the $g^{th}$ nucleotide base of the reference genome as a first set of cp-bases;
   assigning a first subset of the first set of c-bases and a second subset of the first set of cp-bases to the $g^{th}$ nucleotide base of the reference genome, comprising:
      assigning the first subset to the most probable nucleotide bases of the first set of c-bases; and
      assigning the second subset to the most probable oligonucleotide bases of the first set of cp-bases; and
   determining the sequence of the string of nucleotides, comprising:
      setting a first nucleotide base of the string of oligonucleotides equal to the $g^{th}$ nucleotide base of the reference genome, if the first subset is uniquely assigned to the $g^{th}$ nucleotide base of the reference genome; and
      setting a second nucleotide base of the string of oligonucleotides equal to the $g^{th}$ nucleotide base if the second subset is uniquely assigned to the $g^{th}$ nucleotide base of the reference genome.

9. The method of claim 8, wherein assigning the first subset of the first set of c-bases to the $g^{th}$ nucleotide base of the reference genome and the second subset of the first set of cp-bases to the $g^{th}$ nucleotide base of the reference genome comprises:
   generating the first subset comprising the most probable nucleotide bases that are associated with a maximum vote among the unique class U, the double class D, and the triple class T for a nucleotide base of the first set of c-bases; and
   generating the second subset comprising the most probable nucleotide bases that are associated with a maximum vote among the unique class U, the double class D, and the triple class T for a nucleotide base of the first set of cp-bases.

10. The method of claim 7, wherein obtaining the sequence of the string of oligonucleotides by iteratively re-sequencing the mapped sequences pairs set comprises a procedure comprising:
   denoting nucleotide bases of the mapped sequences pairs set by generating a set $R_g$ of c-bases and a set $R_g^*$ of cp-bases for each nucleotide base g of the reference genome, wherein g is within $\{1, \ldots, G\}$, and G represents a length of the reference genome, c-bases comprising a set of nucleotide bases within the mapped read sequences of the mapped sequences pairs set that are aligned to the nucleotide base g of the reference genome and cp-bases comprising a set of nucleotide bases within the mapped read-pair sequences of the mapped sequences pairs set that aligned sequences cover the nucleotide base g of the reference genome;

setting a subset $V_g$ of the $R_g$ by calculating a maximum vote between nucleotide bases of $R_g$, the subset $V_g$ comprising maximum voted c-bases of the $R_g$;

updating the subset $V_g$, comprising:
  setting a re-sequenced nucleotide base g of the string of oligonucleotides equal to the nucleotide base g of the reference genome if the $|V_g|=1$, wherein $|V_g|$ represents size of $V_g$; and
  removing nucleotide base $V_h$, from $V_g$ if $|V_h|=1$ and $|V_g|\neq 1$, wherein:
    $V_h$ comprises a plurality of sets for each h,
    h comprises the corresponding nucleotide base within all read-pair sequences corresponding to read sequences comprising nucleotide base g,
    the procedure iterates for all nucleotide bases within the reference genome if no update occurs in $V_g$, $V_g$ is assigned to nucleotide base g of the reference genome, and
    the procedure ceases if no new nucleotide base of the string of oligonucleotides is updated or all nucleotide bases of the string of oligonucleotides are uniquely determined.

11. The method of claim 1, wherein the string of oligonucleotides and the reference genome comprises an equal number of nucleotide bases represented as G.

12. The method of claim 1, wherein generating the reads pairs set comprises generating a plurality of reads pairs, each reads pair comprising the read and the corresponding read-pair with a distance from each other equal to the pre-defined insert size distance along the string of oligonucleotides.

13. The method of claim 1, wherein generating the reads pairs set comprises generating a plurality of reads pairs with each reads pair of the reads pairs set comprising at least 50 nucleotide bases.

14. A paired-end sequencing method for sequencing a target genome comprising a string of oligonucleotides, the method comprising:
  preparing a template comprising a plurality of wells, each well containing a pair of strands from the target genome, the pair of strands comprising a forward strand and a corresponding reverse strand with an insert size distance from each other along the target genome, the insert size distance being in a range between 100 nucleotide bases and 1000 nucleotide bases;
  generating a reads pairs set comprising a plurality of reads pairs by simultaneously sequencing the pair of strands within each well, each reads pair comprising a read associated with the forward strand of the well and a corresponding read-pair associated with the reverse strand of the well, comprising detecting fluorescence intensity of hybridized nucleotide bases along the forward strand and the corresponding reverse strand at the same time in each well; and
  processing the reads pairs set, comprising:
    generating a sequences pairs set comprising a plurality of sequences pair, each sequences pair comprising a read sequence and a read-pair sequence corresponding to a reads pair of the reads pairs set, comprising:
    classifying each pair of nucleotide bases of each reads pair within one of three classes, the three classes comprising:
      a unique class U comprising a set of pairs of nucleotide bases with a unique possibility for each nucleotide base;
      a double class D comprising a set of pairs of nucleotide bases with two possibilities for each nucleotide base; and
      a triple class T comprising a set of pairs of nucleotide bases with three possibilities for each nucleotide base; and
    detecting each pair of nucleotide bases of the read and the corresponding read-pair of each reads pair within one of the three classes based on the detected fluorescence intensities;
  generating a mapped sequences pairs set by mapping the sequences pairs set along a reference genome, comprising:
    searching for each sequences pair of the sequences pairs set along the reference genome by considering nucleotide bases of the sequences pair classified in the unique class U;
    locating the read sequence and read-pair sequence of the searched sequences pair along the reference genome by retaining nucleotide bases of the searched sequences pair classified in the unique class U and positioning an ambiguous character at nucleotide bases of the searched sequences pair classified in at least one of the double class D or triple class T;
    aligning the located sequences pair along the reference genome responsive to the read sequence and the read-pair sequence being associated with a distance equal to the pre-defined insert size distance by matching nucleotide bases of the located sequences pair to corresponding nucleotide bases of the reference genome; and
    accepting the aligned sequences pair along the reference genome responsive to nucleotide bases of the aligned sequences pair classified in one of the double class D or the triple class T being consistent with corresponding nucleotide bases of the reference genome; and
  obtaining a sequence of the target genome by iteratively re-sequencing the mapped sequences pairs set, comprising determining not accepted nucleotide bases of each aligned sequences pair of the aligned sequences pair set based on nucleotide bases of other aligned sequences pairs of the aligned sequences pair set.

15. The method of claim 14, wherein sequencing the target genome is carried out using a procedure, the procedure comprising:
  classifying nucleotide bases for each corresponding pair of nucleotide bases within a read and a corresponding read-pair of the reads pairs set by determining three sets for each sequences pair $r_i$ from the sequences pairs set $r \{r_1, r_2, \ldots r_i, \ldots, r_N, r_1^*, \ldots, r_N^*\}$, the three sets comprising the unique class $U(r_i)$, the double class $D(r_i)$ and the triple class $T(r_i)$;
  initializing a set S $\{S_{(r1)}, S_{(r2)}, S_{(ri)}, \ldots S_{(rN)}\}$ equal to zero (Ø), wherein $S_{(ri)}$ comprises the mapped sequences pairs set that comprises a set of strings and corresponding locations on the reference genome for each read sequence $r_i$;

searching for each sequences pair of the sequences pairs set along the reference genome and locating the read sequence and read-pair sequence of the searched sequences pair along the reference genome by generating a set $\hat{r}\{\hat{r}_1, \ldots, \infty, \ldots, \hat{r}_N\}$ respective to the set r by retaining the set U ($r_i$) and setting other nucleotide bases as N;

aligning the located sequences pair along the reference genome by aligning the set $\hat{r}$ to the reference genome using an algorithm based on a Burrows-Wheeler Transform (BWT) to find the mapped sequences pairs set for $r_i$;

updating the set S by updating each $S_{(ri)}$, comprising:
  sorting and saving the mapped sequences pairs set for each $r_i$ as , $S_{(ri)}$, wherein the location of a $m^{th}$ string is represented by $l_{S(m)}$, and m is within a set of $\{1, \ldots m, \ldots, |S|\}$ and $|S|$ the size of $S_{(ri)}$, and
  generating a mapped sequences pairs set by accepting the aligned sequences pair along the reference genome responsive to nucleotide bases of the aligned sequences pair that are classified in one of the double class D or the triple class T being consistent with corresponding nucleotide bases of the reference genome, comprising:
    setting a parameter E to be equal to a Hamming distance of each S(j) and $r_i$ in $D_{(ri)}$ and $T_{(ri)}$ locations if the distance between a $l_{S(j)}$ and the next $l_{S(k)}$ is$\geq$D-$\Delta$, wherein j is within $\{1, \ldots, |S|\}$,k is within $\{j+1, \ldots, |S|\}$, D represents an average of the pre-defined insert size distance, and $\Delta$ represents a variance of the pre-defined insert size distance; and
    adding $\{(S_{(j)}, l_{S(j)}), (S_{(k)}, I_{S(k)})\}$ to $S_{(ri)}$ if E$\leq$2, wherein updating the $S_{(ri)}$ ceases if the distance between a $l_{S(j)}$ and next $l_{S(k)}$ is>D+$\Delta$;

denoting nucleotide bases of the mapped sequences pairs set by-generating a set $R_g$ of c-bases and a set $R_g^*$ of cp-bases for each nucleotide base g of the reference genome, wherein g is within $\{1, \ldots, G\}$, and G represents a length of the reference genome, c-bases comprising a set of nucleotide bases within the mapped read sequences of the mapped sequences pairs set that are covered the nucleotide base g of the reference genome and cp-bases comprising a set of nucleotide bases within the mapped read-pair sequences of the mapped sequences pairs set that are covered the nucleotide base g of the reference genome;

setting a subset $V_g$ of the $R_g$ by calculating a maximum vote between nucleotide bases of $R_g$, the subset $V_g$ comprising maximum voted c-bases of the $R_g$;

updating the subset $V_g$, comprising:
  setting a re-sequenced nucleotide base g of the target genome equal to the nucleotide base g of the reference genome if the $|V_g|$=1, wherein $|V_g|$ represents size of $V_g$; and
  removing nucleotide base $V_h$ from $V_g$ if $|V_h|$=1 and $|V_g|\neq 1$ wherein:
    $V_h$ comprises a plurality of sets for each h,
    h comprises the corresponding nucleotide base within all read-pair sequences corresponding to read sequences comprising nucleotide base g,
    the procedure iterates for all nucleotide bases within the reference genome if no update occurs in $V_g$,
    $V_g$ is assigned to nucleotide base g of the target genome, and
    the procedure ceases if no new nucleotide base of the target genome is updated or all nucleotide bases of the target genome are uniquely determined.

* * * * *